United States Patent
Shoemaker

(10) Patent No.: US 11,806,057 B2
(45) Date of Patent: Nov. 7, 2023

(54) SYSTEM AND METHOD FOR SURGICAL IMPLANT POSITIONING AND FIXATION

(71) Applicant: Scott D. Shoemaker, Poway, CA (US)

(72) Inventor: Scott D. Shoemaker, Poway, CA (US)

( * ) Notice: Subject to any disclaimer, the term of this patent is extended or adjusted under 35 U.S.C. 154(b) by 200 days.

(21) Appl. No.: 17/072,928

(22) Filed: Oct. 16, 2020

(65) Prior Publication Data
US 2021/0113249 A1  Apr. 22, 2021

Related U.S. Application Data

(60) Provisional application No. 62/916,679, filed on Oct. 17, 2019.

(51) Int. Cl.
| | | |
|---|---|---|
| *A61B 17/80* | (2006.01) | |
| *A61B 17/02* | (2006.01) | |
| *A61B 17/86* | (2006.01) | |
| *A61B 17/90* | (2006.01) | |
| *A61B 34/20* | (2016.01) | |
| *A61L 31/06* | (2006.01) | |
| *A61B 17/00* | (2006.01) | |
| *A61B 90/00* | (2016.01) | |

(52) U.S. Cl.
CPC ............ *A61B 17/808* (2013.01); *A61B 17/02* (2013.01); *A61B 17/86* (2013.01); *A61B 34/20* (2016.02); *A61L 31/06* (2013.01); *A61B 17/90* (2021.08); *A61B 2017/00557* (2013.01); *A61B 2034/2072* (2016.02); *A61B 2090/0807* (2016.02)

(58) Field of Classification Search
CPC ....... A61B 17/808; A61B 17/02; A61B 17/86; A61B 17/90; A61B 17/1728; A61B 17/3468; A61B 17/3472; A61B 17/3423; A61B 2090/0807; A61B 2017/0057; A61B 17/8872
See application file for complete search history.

(56) References Cited

U.S. PATENT DOCUMENTS

| 205,990 | A | 7/1878 | Armstrong |
| 3,177,755 | A | 4/1965 | Kahn |
| 6,322,562 | B1 | 11/2001 | Wolter |
| 6,602,027 | B2 | 8/2003 | Deaton et al. |
| 7,695,228 | B2 | 4/2010 | Craven |
| 7,736,305 | B2 * | 6/2010 | DiPoto ............... A61B 17/7044 600/201 |

(Continued)

*Primary Examiner* — Tracy L Kamikawa
(74) *Attorney, Agent, or Firm* — ROEDER & BRODER LLP; James P. Broder

(57) ABSTRACT

A positioning device for positioning an orthopedic implant in a patient during a surgical procedure includes a first orthopedic fastener and a device body. The orthopedic fastener penetrates into a bone of the patient to secure the orthopedic implant to the bone. The device body is removably positionable at least partially subcutaneously within the patient. The device body can retract tissue of the patient and includes a first fastener guide that guides positioning of the first orthopedic fastener relative to the bone of the patient. The device body releasably secures the orthopedic implant during positioning of the orthopedic implant. The positioning device can also include an implant attacher that removably secures the orthopedic implant to the device body. The implant attacher movably extends through the device body along an attacher axis.

12 Claims, 8 Drawing Sheets

(56) References Cited

U.S. PATENT DOCUMENTS

| | | | |
|---|---|---|---|
| 7,811,312 B2 * | 10/2010 | Stevens | A61B 17/8061 |
| | | | 623/13.12 |
| 8,052,729 B2 * | 11/2011 | Dube | A61B 17/1728 |
| | | | 606/280 |
| 8,133,230 B2 | 3/2012 | Stevens et al. | |
| 8,403,968 B2 * | 3/2013 | Rabiner | A61B 17/8085 |
| | | | 606/283 |
| 8,523,862 B2 * | 9/2013 | Murashko, Jr. | A61B 17/1728 |
| | | | 606/71 |
| 8,641,742 B2 | 2/2014 | Stevens et al. | |
| 8,652,180 B2 * | 2/2014 | Federspiel | A61B 17/1728 |
| | | | 606/915 |
| 8,998,550 B2 | 4/2015 | Platt | |
| 9,408,647 B2 | 8/2016 | Cheney | |
| 9,532,825 B2 * | 1/2017 | Geebelen | A61B 17/1739 |
| 2002/0085890 A1 | 7/2002 | Bandeian, III et al. | |

* cited by examiner

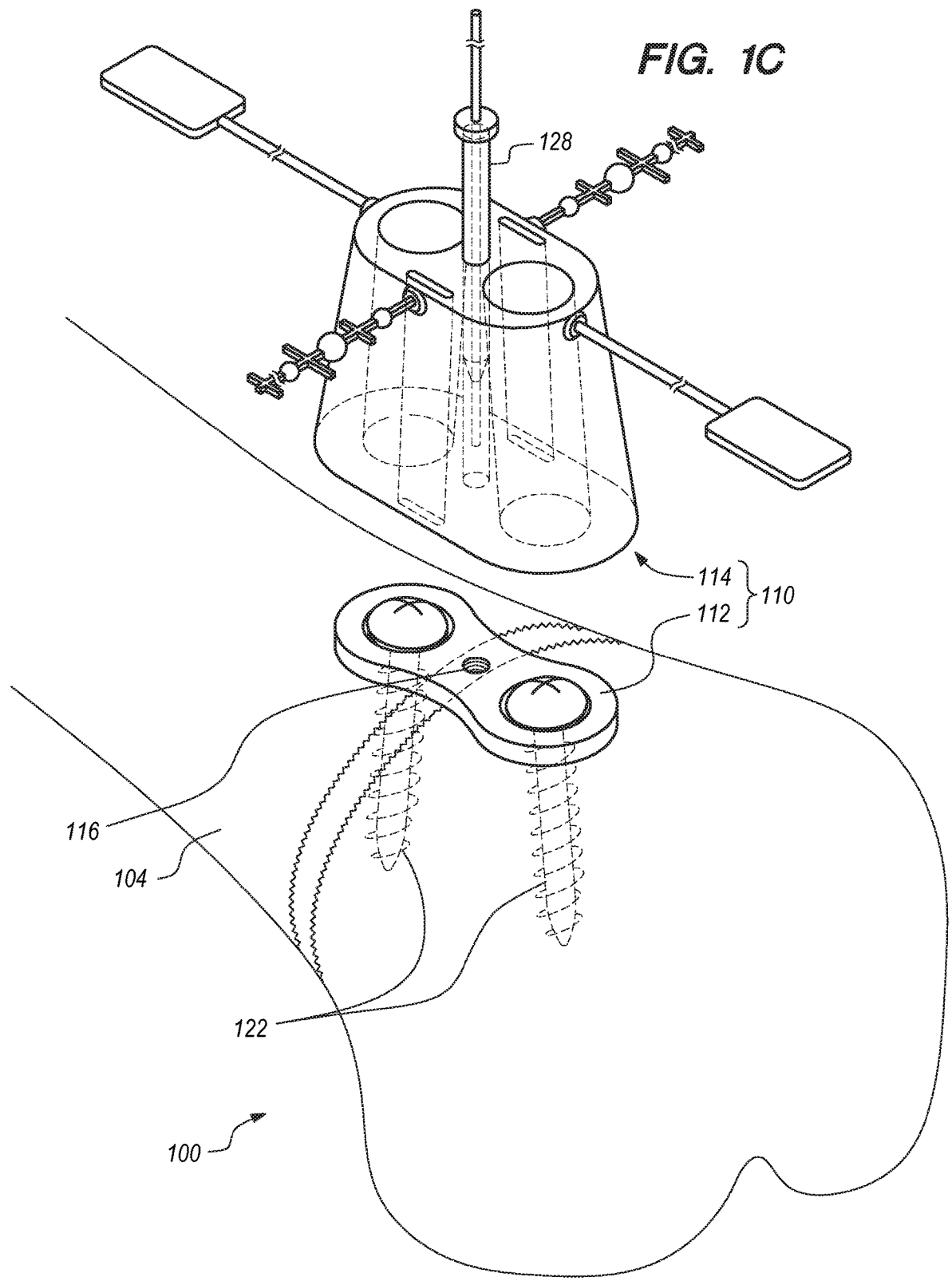

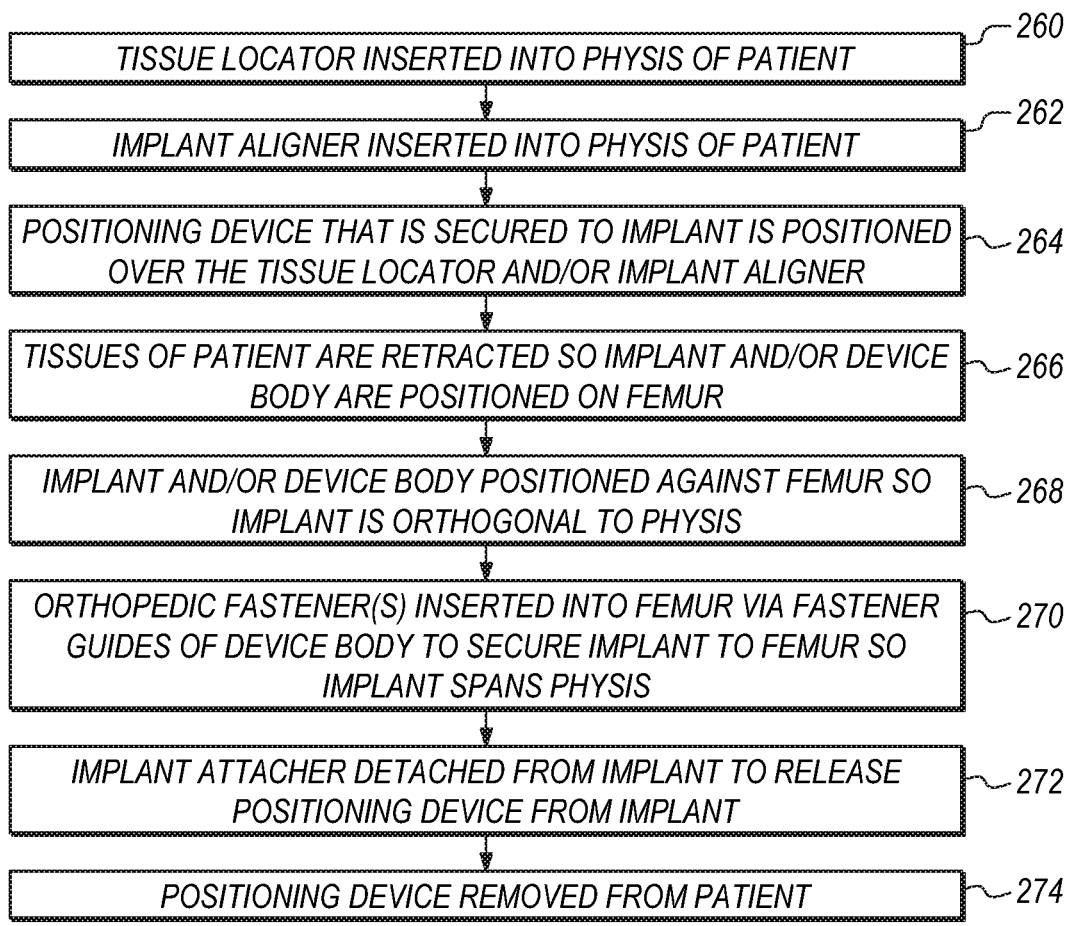

SYSTEM AND METHOD FOR SURGICAL IMPLANT POSITIONING AND FIXATION

RELATED APPLICATION

This application claims priority on U.S. Provisional Application Ser. No. 62/916,679, filed on Oct. 17, 2019, and entitled "SYSTEM AND METHOD FOR SURGICAL IMPLANT INSERTION". As far as permitted, the contents of U.S. Provisional Application Ser. No. 62/916,679 are incorporated in their entirety herein by reference.

BACKGROUND

Stabilizing bones and guiding growth of bones with surgical implants such as metal plates has been the basis of orthopedic surgery for decades. Guiding growth by harnessing the ability of growing bone to undergo plastic deformation is one of the oldest orthopedic principles. Correction of deformity remains a major part of the workload for pediatric orthopedic surgeons. Recently, along with developments in limb reconstruction and computer-directed frame correction, there has been renewed interest in surgical methods of physeal manipulation to guide growth of the bone. Manipulating natural bone growth to correct a deformity is appealing, as it allows gradual correction by minimally invasive means. Growth modulation surgery is one of the most common types of surgery in pediatric orthopedics.

Typically, in order to accomplish this procedure, an orthopedic surgeon (or other medical practitioner) exposes the bone and must retract surrounding tissues to provide the surgeon with necessary and continuous access to the bone. The surgeon then precisely aligns an implant over a specific region of the bone to affix a metal plate to the bone with special screws. This process can take a substantial amount of time and can often cause damage to the surrounding tissues, which can significantly impact the post-operative recovery for the patient.

Additionally, numerous radiographic images are normally taken during various stages of the operation to ensure the metal plate is properly positioned on the bone. The number of images that are typically obtained—some with the surgeon's hands in the field—can be in the dozens, potentially resulting in relatively high radiation to the patient, the surgeon and other medical staff members. Compounding matters, the length of the surgical time is directly correlative to the risk of infection to the patient. Furthermore, the surgery time directly translates to already increasing medical costs. In other words, the longer the surgery, the higher the costs to the patient and medical insurance companies. Accordingly, there is a need to improve precision of the surgery, decrease surgery duration, and lower radiation exposure that is currently required.

SUMMARY

The present invention is directed toward a positioning device for positioning an orthopedic implant in a patient during a surgical procedure. In certain embodiments, the positioning device includes a first orthopedic fastener and a device body. The orthopedic fastener can be configured to penetrate into a bone of the patient to secure the orthopedic implant to the bone. The device body can be removably positionable at least partially subcutaneously within the patient during the surgical procedure. The device body can be configured to retract tissue of the patient during the surgical procedure. The device body can include a first fastener guide that is configured to guide positioning of the first orthopedic fastener relative to the bone of the patient.

In various embodiments, the device body can be configured to releasably secure the orthopedic implant during positioning of the orthopedic implant in the patient.

In some embodiments, the device body can be inflatable

In certain embodiments, the positioning device also includes an implant attacher that removably secures the orthopedic implant to the device body. In some such embodiments, the implant attacher movably extends through the device body along an attacher axis.

In various embodiments, the positioning device also includes a tissue locator that movably extends through the implant attacher along the attacher axis.

In some embodiments, the first fastener guide is angled at least 3 degrees relative to the attacher axis.

In certain embodiments, the positioning device can include a second orthopedic fastener. In some such embodiments, the device body can include a second fastener guide so that the fastener guides are positioned on opposing sides of the implant attacher. In various embodiments, each fastener guide can be configured to guide positioning of one corresponding orthopedic fastener relative to the bone of the patient.

In various embodiments, at least two of the fastener guides are non-parallel to one another.

In some embodiments, the implant attacher includes threads that selectively engage the orthopedic implant to removably secure the orthopedic implant to the device body.

In certain embodiments, the orthopedic implant can be a growth plate.

In various embodiments, the orthopedic fastener is threaded and/or can be a Torx screw.

In some embodiments, the positioning device can include a body positioner that is coupled to the device body. The body positioner can have visual indicia to position the device body relative to the bone of the patient.

In certain embodiments, the positioning device can include a body positioner that is coupled to the device body. The body positioner can be configured to cooperate with an imaging system to position the device body relative to the bone of the patient.

In various embodiments, the device body has a somewhat frustoconical configuration or a cylindrical configuration.

In some embodiments, the orthopedic implant can be formed from metal or a polyester fiber material.

The present invention is also directed toward a positioning device that includes a device body that is removably positionable at least partially subcutaneously within the patient during the surgical procedure. In some embodiments, the device body is configured to retract tissue of the patient during the surgical procedure. The device body can include a pair of fastener guides that are each configured to guide positioning of a corresponding orthopedic fastener relative to the bone of the patient.

In various embodiments, the positioning device can include an implant attacher that removably secures the orthopedic implant to the device body. The implant attacher can movably extend through the device body along an attacher axis.

The present invention is also directed toward one or more methods for surgical implant positioning, fixation and/or removal.

The present invention is also directed toward a positioning device for positioning an orthopedic implant in a patient during a surgical procedure. In certain embodiments, the positioning device can include two orthopedic fasteners, a device body, and a body attacher. The two orthopedic fasteners are each configured to penetrate into a bone of the patient to secure the orthopedic implant to the bone. At least one of the orthopedic fasteners is threaded. The device body can be removably positionable at least partially subcutaneously within the patient during the surgical procedure. The device body can be configured to retract tissue of the patient during the surgical procedure. The device body can be configured to releasably secure the orthopedic implant during positioning of the orthopedic implant in the patient. The device body can include two fastener guides that are each configured to guide positioning of one of the orthopedic fasteners relative to the bone of the patient. The fastener guides can be non-parallel to one another. The body attacher removably attaches the device body to the patient. The body attacher can movably extend through the device body along an attacher axis that is approximately orthogonal relative to the bone of the patient.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which:

FIG. 1C is a perspective view of a portion of the patient and the orthopedic implant positioning system illustrated in FIG. 1A, the orthopedic implant being shown in a detached position relative to the orthopedic implant positioning device;

FIG. 2 is a flow chart describing one embodiment of a method for surgical implant positioning and/or fixation.

While embodiments of the present invention are susceptible to various modifications and alternative forms, specifics thereof have been shown by way of example and drawings, and are described in detail herein. It is understood, however, that the scope herein is not limited to the particular embodiments described. On the contrary, the intention is to cover modifications, equivalents, and alternatives falling within the spirit and scope herein.

DESCRIPTION

Those of ordinary skill in the art will realize that the following detailed description of the present invention is illustrative only and is not intended to be in any way limiting. Other embodiments of the present invention will readily suggest themselves to such skilled persons having the benefit of this disclosure. Reference will now be made in detail to implementations of the present invention as illustrated in the accompanying drawings.

In the interest of clarity, not all of the routine features of the implementations described herein are shown and described. It will, of course, be appreciated that in the development of any such actual implementation, numerous implementation-specific decisions must be made in order to achieve the developer's specific goals, such as compliance with application-related and business-related constraints, and that these specific goals will vary from one implementation to another and from one developer to another. Moreover, it is appreciated that such a development effort might be complex and time-consuming, but would nevertheless be a routine undertaking of engineering for those of ordinary skill in the art having the benefit of this disclosure.

As an overview, in one embodiment, the device and method shown and/or described herein is applied to guided growth surgery in pediatric orthopedics. Guiding growth by harnessing the ability of growing bone to undergo plastic deformation is one of the oldest orthopedic principles. Correction of deformity remains a major part of the workload for pediatric orthopedic surgeons and recently, along with developments in limb reconstruction and computer-directed frame correction, there has been renewed interest in surgical methods of physeal manipulation or 'guided growth'. Manipulating natural bone growth to correct a deformity is appealing, as it allows gradual correction by minimally invasive means.

Figure 1A:
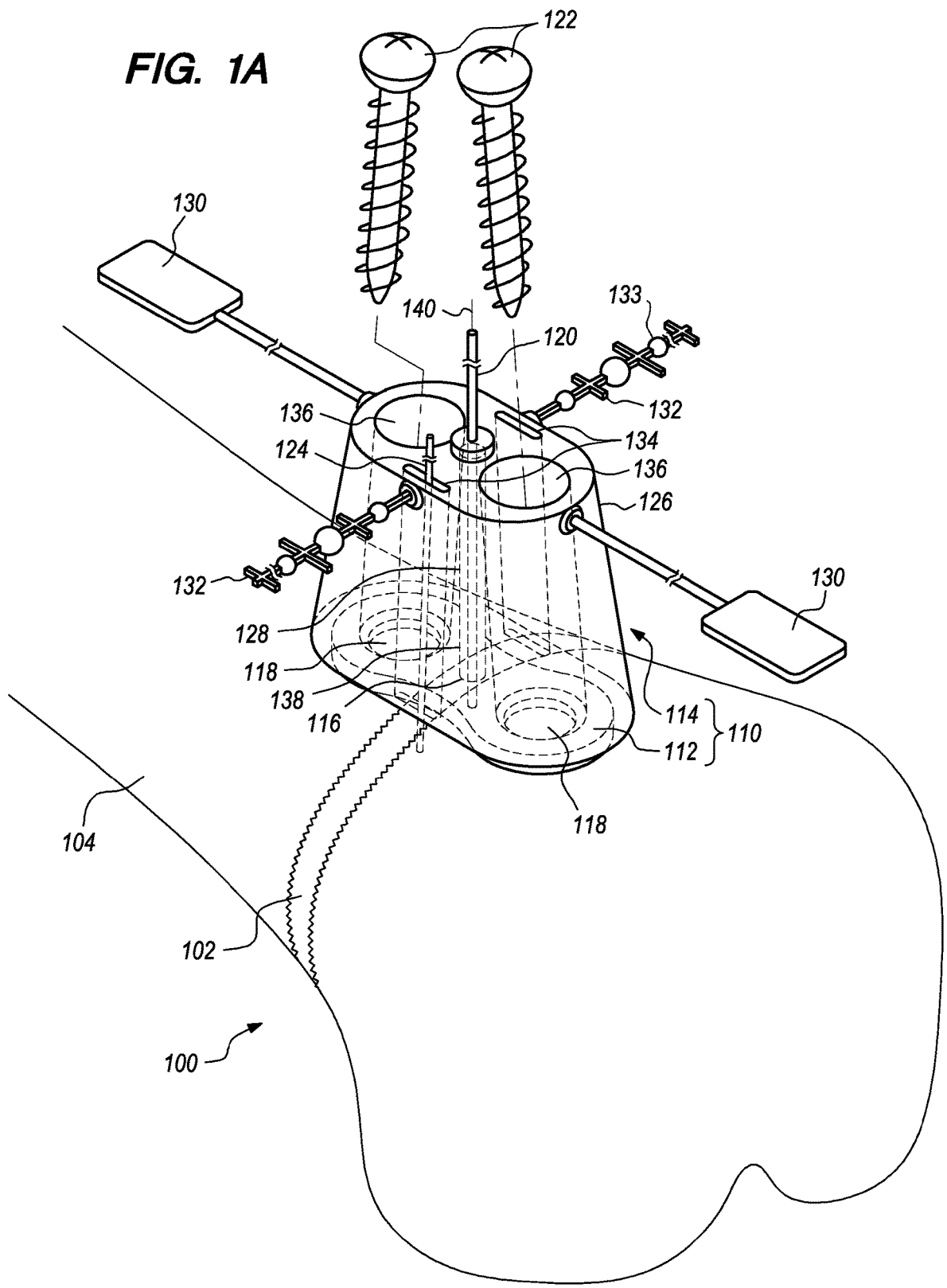
FIG. 1A is a perspective view of a portion of a patient and one embodiment of an orthopedic implant positioning system having features of the present invention, including an orthopedic implant and an orthopedic implant positioning device, the orthopedic implant being shown in an attached position relative to the orthopedic implant positioning device.

FIG. 1A is a perspective view of a portion of a patient 100, and an orthopedic implant positioning system 110 (sometimes hereinafter referred to simply as a "positioning system"). The orthopedic implant positioning system 110 can be used in various orthopedic surgical procedures to repair, correct, guide and/or steer various orthopedic structures in the body of the patient 100. Additionally, or in the alternative, the orthopedic implant positioning system 110 can be used in various orthopedic surgical procedures following repair, etc., of the orthopedic structures. The design of the orthopedic implant positioning system 110 can be varied depending upon the specific orthopedic structures involved.

In the embodiment illustrated in FIG. 1A, the orthopedic implant positioning system 110 includes an orthopedic implant 112 (illustrated in phantom and hereinafter sometimes referred to simply as an "implant") and an orthopedic implant positioning device 114 (hereinafter sometimes referred to simply as a "positioning device"). In the embodiment illustrated in FIG. 1A, the implant 112 is shown in an attached position relative to the positioning device 114. Although the description herein focuses primarily on a physis 102 of a femur 104 of the patient 100, and on controlling growth of the femur 104, it is understood that the orthopedic implant positioning system 110 (and described methods herein) can be used to place orthopedic implants 112 for repair, correction or fracture work at any suitable anatomical region of the body of the patient 100. Stated another way, the description of the orthopedic implant positioning system 110 relative to the physis 102 of the femur 104 is not intended to be limiting in any manner, but rather serves to be representative of the types of procedures in which the orthopedic implant positioning system 110 can be used. As used herein, the term "femur" and "bone" can be used interchangeably, although it is understood that the term "bone" can include bones other than the femur.

In various embodiments, the implant 112 is secured to the femur 104 of the patient 100 during the orthopedic surgical procedure. The implant 112 can influence or otherwise control growth of the femur 104 (including the physis 102) depending upon the needs of the patient 100. In the embodiment illustrated in FIG. 1A, the implant 112 can include a rigid plate having one or more physis positioner apertures 116 and/or one or more fastener receivers 118. The implant 112 illustrated in FIG. 1A is somewhat figure-8 shaped, and includes one physis positioner aperture 116 and two fastener apertures 118. Alternatively, the implant 112 can include greater or fewer than one physis positioner aperture 116, and/or greater or fewer than two fastener apertures 118. The implant 112 can have any suitable configuration that suits the design requirements of the orthopedic implant positioning system 110 and/or the needs of the patient 100.

The physis positioner aperture 116 is configured to be positioned relative to the femur 104 of the patient 100 so that the physis positioner aperture 116 is directly over the physis 102. The physis positioner aperture 116 selectively receives a tissue locator 120 that extends through at least a portion of the positioning device 114 to the desired tissue, such as the physis 102, as described in greater detail herein. With this design, the implant 112 can be properly positioned relative to the physis 102 of the femur 104 during the surgical procedure. In one embodiment, the physis positioner aperture 116 can be centrally located on the implant 112. In certain embodiments, the physis positioner aperture 116 can be positioned directly between and/or equidistant from at least two of the fastener receivers 118 in embodiments that include at least two fastener receivers 118.

The fastener receivers 118 are each configured to receive one orthopedic fastener 122 that then extends into the femur 104 of the patient 100. As used herein the orthopedic fasteners 122 can be referred to as a "first orthopedic fastener", a "second orthopedic fastener", etc. It is understood that this is for ease of discussion only, and that any orthopedic fastener can be the first orthopedic fastener, the second orthopedic fastener, etc.

The fastener receivers 118 can be either threaded or non-threaded. In various embodiments, the fastener receivers 118 can be angled or otherwise configured to generate compression (or tension) in the femur 104 as desired depending upon the needs of the patient 100 following placement of the orthopedic fasteners 122.

In certain embodiments, the implant 112 can be partially or entirely formed from a metal material that provides sufficient rigidity on its own. Alternatively, the implant 112 can be at least partially formed from another suitably rigid material, such as ceramics, composites, or any another suitable material or materials. Still alternatively, the implant 112 can be formed from a flexible and/or resilient material. Further, the dimensions of the implant 112 can be varied to suit the design parameters of the positioning system 110 and/or the needs of the patient 100.

The orthopedic implant positioning device 114 can serve one or more of a variety of functions. For example, in various non-exclusive embodiments, during the orthopedic surgical procedure, the positioning device 114 can, without limitation, retract skin 142 (illustrated in FIG. 1E) and/or various other tissues of the patient 100, can guide the orthopedic fasteners 122 to extend into and through the fastener receivers 118 and into the femur 104, can releasably secure and/or position the implant 112, can facilitate use of an imaging system 148 (illustrated in FIG. 1F) to more accurately position the implant 112, and/or can locate previously positioned implants 112 and their respective orthopedic fasteners 122 so that a previously-placed implant 112 can be more quickly and effectively removed, among other functions. Two or more of the aforementioned functions can be performed concurrently during use of the positioning device 114.

The design, configuration and/or functionality of the positioning device 114 can vary. In the embodiment illustrated in FIG. 1A, the positioning device 114 can include one or more of the tissue locator 120, one or more of the orthopedic fasteners 122 (two orthopedic fasteners 122 are illustrated in FIG. 1A), one or more implant aligners 124 (one implant aligner 124 is illustrated in FIG. 1A), a device body 126, an implant attacher 128, one or more positioner handles 130, and/or one or more body positioners 132.

The tissue locator 120 can first be used to locate the physis 102, prior to positioning the remainder of the positioning system 110. Once the tissue locator 120 is positioned at the physis 102, the positioning system 110 can be positioned over the tissue locator 120 so that the tissue locator 120 extends through the implant attacher 128 which is positioned at least partially within the device body 126.

The specific design of the tissue locator 120 can vary. In one embodiment, the tissue locator 120 can extend through the implant attacher 128 along an attacher axis 140 of the implant attacher 128. Alternatively, the tissue locator 120 can extend through the device body 126 via an aperture or structure other than the implant attacher 128. Non-exclusive examples of the tissue locator 120 can include a K-wire, a needle or another suitably rigid structure (wire or otherwise) that can contact the physis 102 without damaging such tissue. In one embodiment, the tissue locator 120 can be threaded. Alternatively, the tissue locator 120 can be non-threaded. Because the physis 102 is somewhat softer and less rigid than the boney portion of the femur 104, a user of the positioning system 110 can insert the tissue locator 120 through the device body 126 to check the relative hardness or softness of the femur 104 in order to locate the physis 102.

The implant aligner 124 cooperates with the tissue locator 120 to define the location/orientation of the physis 102 so that proper placement of the implant 112 can be achieved. Any number of implant aligners 124 can be used to determine the orientation of the physis 102. In one embodiment, the implant aligner 124 can extend through at least a portion of the device body 126 to locate the physis 102. Non-exclusive examples of the implant aligner 124 can include a K-wire, a needle or another suitably rigid structure (wire or otherwise) that can contact the physis 102 without damaging such tissue. The implant aligner 124 and the tissue locator 120 define a line that establishes an orientation of the physis 102. Once the orientation of the physis 102 has been established by the implant aligner 124 and the tissue locator 120, the device body 126 can be rotated so that the fastener receivers 118 of the implant 112 span over either side of the physis 102. In this manner, the orthopedic fasteners can be inserted into the femur 104 on either side of the physis 102 without damaging the physis 102.

The device body 126 can retract the tissues (skin, connective tissue, muscle, adipose tissue, etc.) of the patient so that the implant 112 can be properly positioned relative to the femur 104. Additionally, the device body 126 provides guidance for the orthopedic fasteners 122 that secure the implant 112 to the femur 104. The design of the device body 126 can vary. In one embodiment, the device body 126 can have a somewhat frustoconical configuration such that a portion of the device body that is positioned subcutaneously (within the patient 100) has a larger footprint that that which extends outside of the patient 100. Alternatively, the device body 126 can have a somewhat cylindrical configuration, an hourglass configuration, a pyramidal configuration, a diamond-shaped configuration, or any other suitable configuration so that the device body can serve one or more of the purposes disclosed herein.

The device body 126 can be formed from any suitable materials, such as metal, ceramic, composite materials, various plastics, compostable materials or rubberized materials, or another suitable material or combination of materials. In an alternative embodiment, the device body can be inflatable so that retraction of the tissues necessary for the orthopedic surgical procedure can be better controlled and a smaller incision can be used.

In certain embodiments, the device body 126 can include one or more of one or more aligner apertures 134 (two locator apertures 134 are illustrated in FIG. 1A), one or more fastener guides 136 (two fastener guides 136 are illustrated in FIG. 1A) and an attacher receiver 138.

Each aligner aperture 134 receives and guides a corresponding implant aligner 124 in a direction through the device body 126. The aligner aperture 134 can be any suitable shape or configuration. The positioning of the aligner aperture 134 can vary but should cooperate with the positioning of the tissue locator 120 to establish a line that defines the position of the physis 102.

Each fastener guide 136 guides a corresponding orthopedic fastener 122 through the device body 126 to extend into one of the fastener receivers 118 and into the femur 104 of the patient 100. In one embodiment, the fastener guides 136 can be substantially tubular or cylindrical in configuration. Alternatively, the fastener guides 136 can have a somewhat conical or frustoconical configuration, or any other suitable configuration. In certain embodiments, the fastener guides 136 can be angled relative to one another. Stated another way, the fastener guides 136 can be non-parallel with one another. Alternatively, the fastener guides 136 can be parallel with one another.

The attacher receiver 138 receives the implant attacher 128. At least a portion of the implant attacher 128 is movably positioned within the attacher receiver 138 during at least part of the orthopedic surgical procedure. In certain embodiments, the implant attacher 128 movably extends through the device body 126 along an attacher axis 140. The implant attacher 128 can also, or alternatively, rotate within the attacher receiver 138 as needed. The implant attacher 128 can releasably engage the physis positioner aperture 116 of the implant 112. The implant attacher 128 can thereby releasably secure the implant 112 to the implant attacher 128 and/or the device body 126 during positioning and/or securing of the implant 112 relative to the femur 104 of the patient 100. Once the implant 112 has been positioned, the implant attacher 128 can release the implant 112. In one embodiment, the implant attacher 128 can selectively threadedly secure the implant 112 during positioning and/or securing of the implant 112 to the femur 104. With this design, once the implant 112 has been positioned and/or secured to the femur 104, the implant attacher 128 can be unscrewed from the implant 112.

The positioner handles 130 can be held by the user during positioning of the positioning system 110 relative to the patient 100. The positioner handles 130 can extend away from the positioning device 114 for leverage and/or for the user to more safely position the positioning system 110 while radiographs may be taken so that the user is less subjected to harmful radiation. The positioner handles 130 can be removable or fixed. In one embodiment, at least one of the positioner handles 130 can include glass balls 150 (illustrated in FIG. 1F) or other components that can cooperate with an imaging system 148 (illustrated in FIG. 1F).

The body positioner 132 assists in aligning and/or positioning the device body 126 relative to one or more known structures within the body of the patient 100. The body positioner 132 can serve as a visual aid for the user by including one or more visual indicia that can be used to better position the device body 126, and thus the implant 112 relative to the physis 102 of the femur 104. Additionally, or in the alternative, the body positioner 132 can cooperate with the imaging system 148 (illustrated in FIG. 1F) to better position the device body 126, and thus the implant 112, relative to the femur 104. As shown in FIG. 1A, the body positioner 132 can include visual indicia 133 that positions the device body 126 relative to the physis 102 of the femur 104 of the patient 100.

Figure 1B:
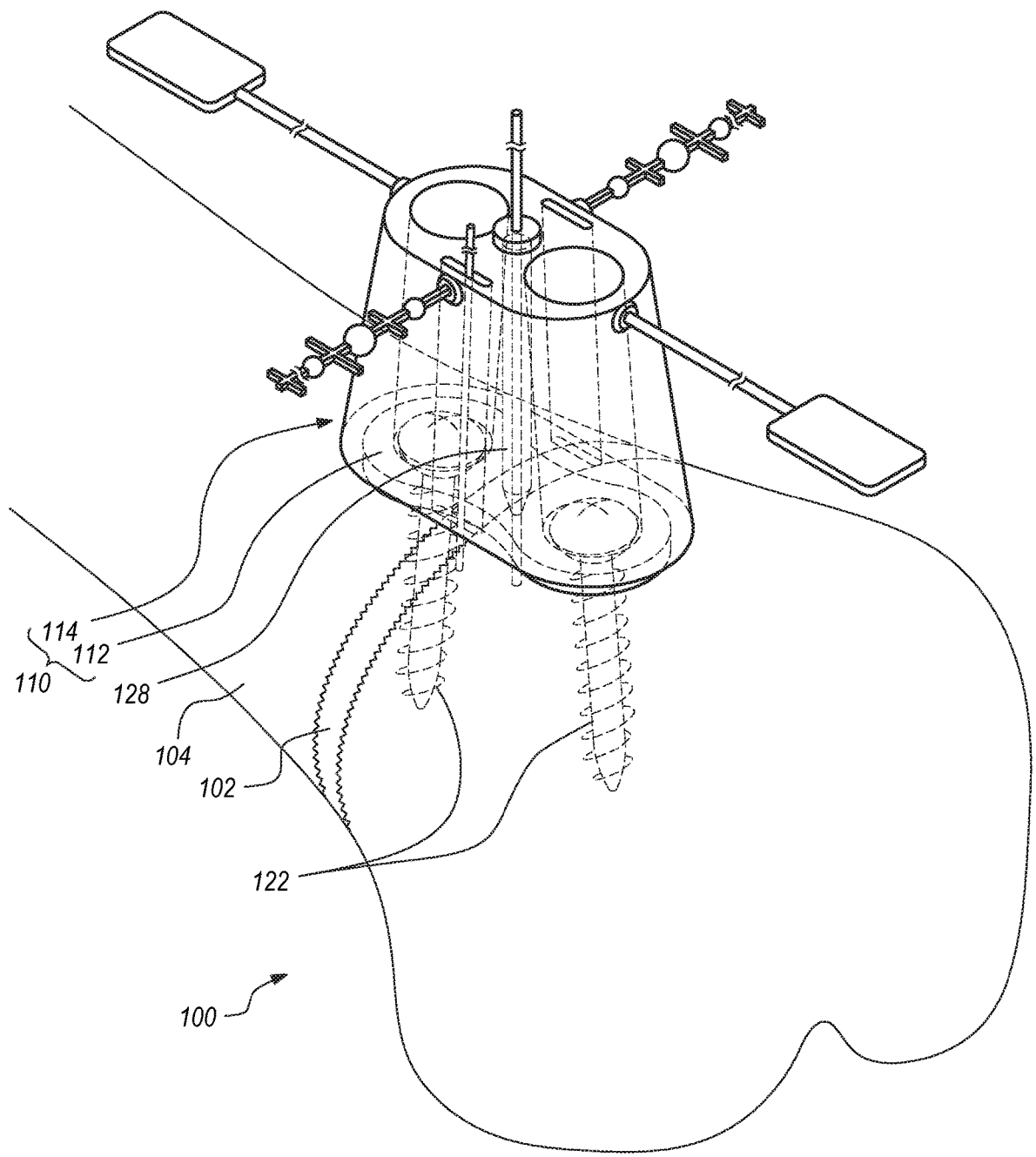
FIG. 1B is a perspective view of a portion of the patient and the orthopedic implant positioning system illustrated in FIG. 1A, the orthopedic implant being shown in an attached position relative to the orthopedic implant positioning device.

FIG. 1B is a perspective view of a portion of the patient 100 and the orthopedic implant positioning system 110 illustrated in FIG. 1A. In the embodiment illustrated in FIG. 1B, the orthopedic implant 112 is shown in an attached position relative to the orthopedic implant positioning device 114. In FIG. 1B, the implant 112 has been positioned relative to the physis 102, and the orthopedic fasteners 122 have been secured to the femur 104. In one embodiment, the orthopedic fasteners 122 can be threadedly secured to the femur 104. Alternatively, the orthopedic fasteners 122 can be secured to the femur 104 by another suitable method. In some embodiments, the orthopedic fastener 122 can include a Torx screw or another suitable type of screw. In one embodiment, the orthopedic fasteners 122 can cooperate with the fastener receivers 118 in a non-locking manner. Alternatively, the orthopedic fasteners 122 can cooperate with the fastener receivers 118 in a locking manner. In the embodiment illustrated in FIG. 1B, the implant attacher 128 is still attached to the implant 112.

FIG. 1C is a perspective view of a portion of the patient 100 and the orthopedic implant positioning system 110 illustrated in FIG. 1A. In FIG. 1C, the orthopedic implant 112 is shown in a detached position relative to the orthopedic implant positioning device 114. In other words, once the orthopedic fasteners 122 have secured the implant 112 to the femur 104, the implant attacher 128 can be unthreaded from the physis positioner aperture 116 of the implant 112, and the positioning device 114 can be removed from the patient 100.

Figure 1D:
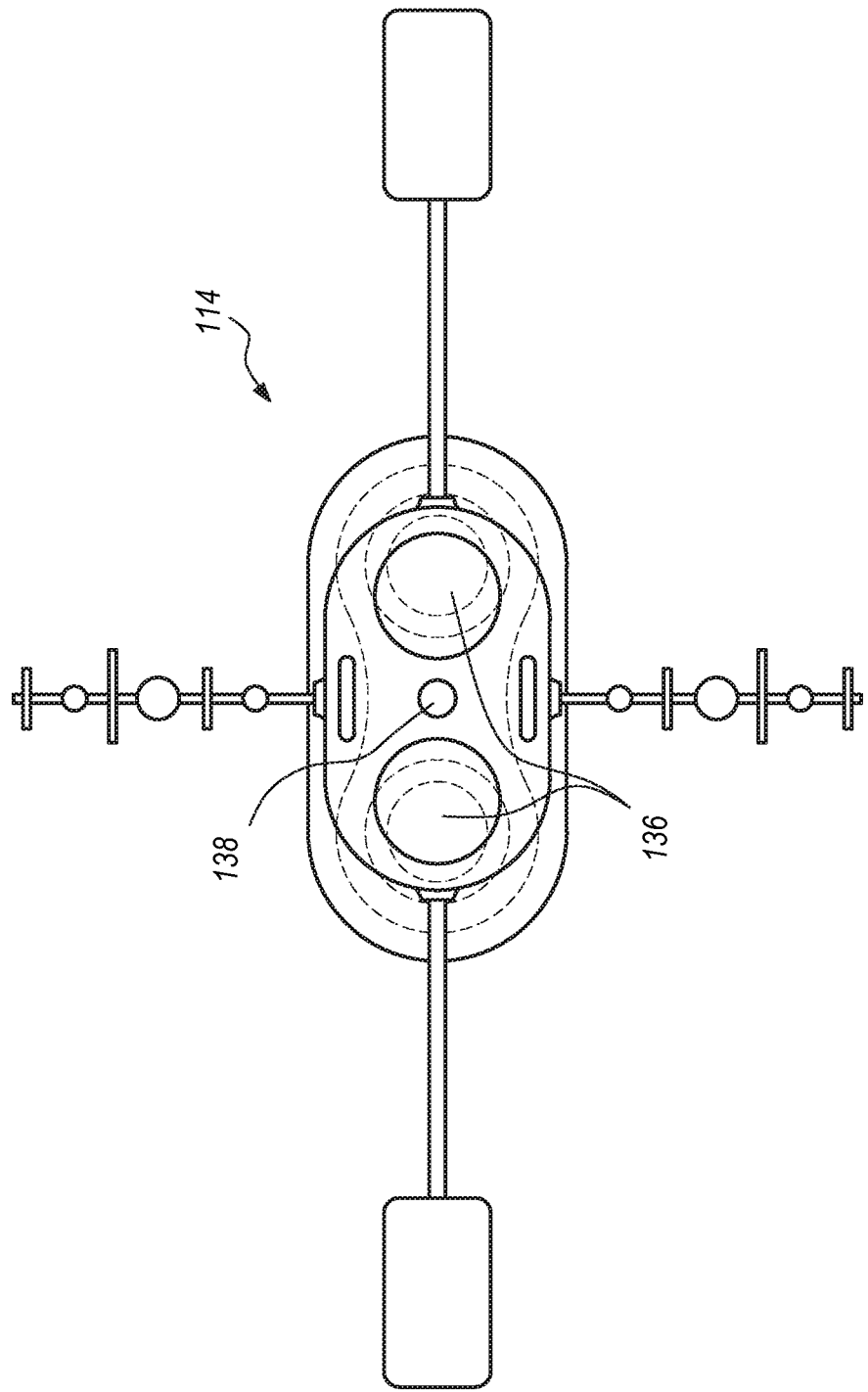
FIG. 1D is a top view of the orthopedic implant positioning device illustrated in FIG. 1A.

FIG. 1D is a top view of a portion of the orthopedic implant positioning device 114 illustrated in FIG. 1A. In the embodiment illustrated in FIG. 1D, the fastener guides 136 are shown angled away from the attacher receiver 138. With this design, the orthopedic fasteners 122 (illustrated in FIG. 1A) will penetrate the femur 104 (illustrated in FIG. 1A) at opposing angles to provide compression of the femur 104. In alternative embodiments, the fastener guides 136 can be angled toward the attacher receiver 138, or can be substantially parallel relative to the attacher receiver 138.

Figure 1E:
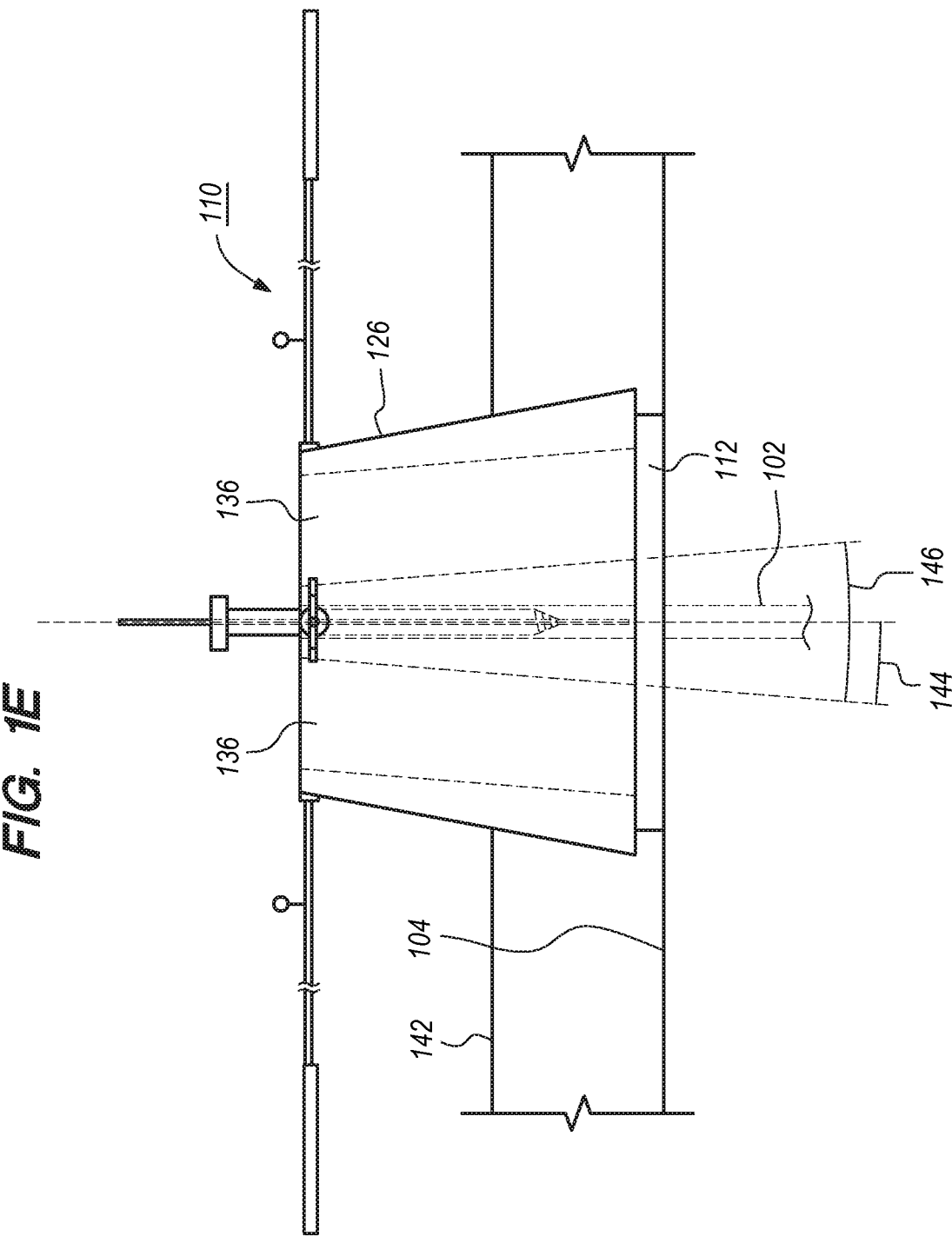
FIG. 1E is a side view of the orthopedic implant positioning device illustrated in FIG. 1A.

FIG. 1E is a side view of a portion of the patient and a portion of the orthopedic implant positioning system 110 illustrated in FIG. 1A. In this embodiment, the device body 126 is illustrated at least partially below a surface of the skin 142 of the patient 100, while the implant 112 is illustrated in contact with the femur 104.

In the embodiment illustrated in FIG. 1E, one or more of the fastener guides 136 can be angled relative to the attacher axis 140. In one embodiment, at least one of the fastener guides 136 can form an angle 144 with the attacher axis that is at least 1 degree. In non-exclusive alternative embodiments, at least one of the fastener guides 136 can form an angle 144 with the attacher axis that is at least 2 degrees, 3 degrees, 5 degrees, 10 degrees, 15 degrees or 20 degrees. Still alternatively, at least one of the fastener guides 136 can form an angle 144 with the attacher axis that is greater than degrees.

In the embodiment illustrated in FIG. 1E, the fastener guides 136 can be angled relative to one another on opposite sides of the physis 102. In one embodiment, the fastener guides 136 can form an angle 146 with one another that is at least 1 degree. In non-exclusive alternative embodiments, the fastener guides 136 can form an angle 146 with one another that is at least 2 degrees, 3 degrees, 5 degrees, 10 degrees, 15 degrees, 20 degrees, 25 degrees, 30 degrees or 45 degrees. Still alternatively, the fastener guides 136 can form an angle 146 with one another that is greater than 45 degrees.

Figure 1F:
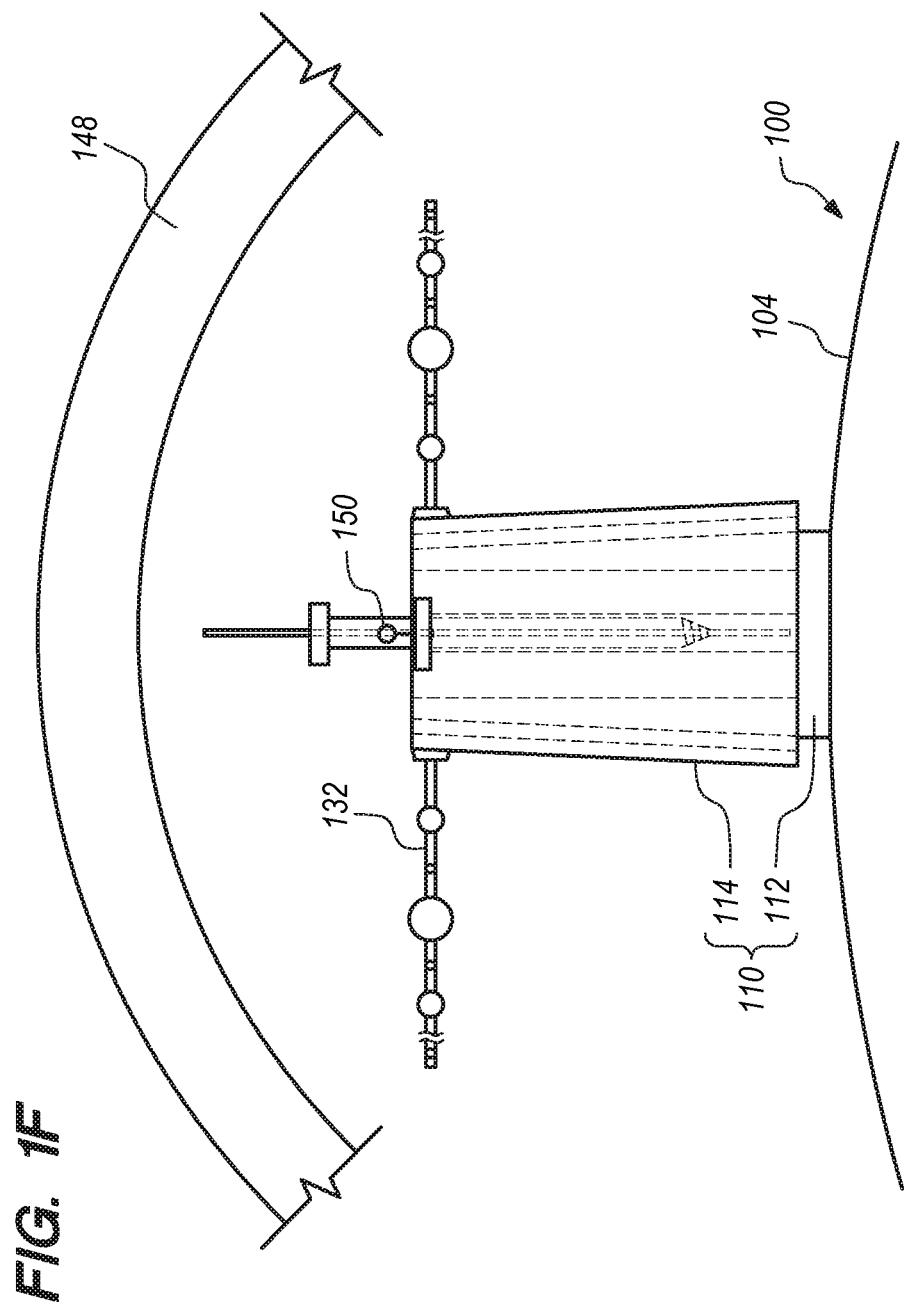
FIG. 1F is a front view of the orthopedic implant positioning device illustrated in FIG. 1A.

FIG. 1F is a front view of a portion of the patient and a portion of the orthopedic implant positioning system 110 illustrated in FIG. 1A. In this embodiment, the positioning system 110 includes the body positioner 132 which cooperates with an imaging system 148 to more accurately position the implant 112 and the positioning device 114 relative to the femur 104 of the patient 100. The imaging system 148 can include any suitable type of system such as an x-ray system, an intraoperative 2D/3D imaging system (such as an O-Arm™ system), CT guidance systems and/or ultrasound.

FIG. 2 is a flow chart describing a method for surgical implant positioning and/or fixation. It is understood that the methods described herein may include additional steps that are not specifically described. Further, the methods described herein may include steps that are described that can be omitted. In one embodiment, the method can include one or more of the following steps.

At step 260, a tissue locator can be inserted and/or threaded into the physis of the patient.

At step 262, an implant aligner can be inserted into the physis to define a line between the tissue locator and the implant aligner.

At step 264, the orthopedic implant positioning device that is secured to an orthopedic implant can be positioned over the tissue locator and/or the implant aligner so that the tissue locator is threaded up through a device body of the positioning device.

At step 266, tissues of the patient can be retracted so that the orthopedic implant and/or a portion of the device body of the positioning device can be positioned on a femur of the patient.

At step 268, the orthopedic implant and/or the device body are properly positioned against the femur so that the orthopedic implant is orthogonal to the physis of the patient.

At step 270, at least one orthopedic fastener is inserted into the femur via fastener guides of device body to secure the orthopedic implant to the femur so that the orthopedic implant spans across the physis of the patient. In one embodiment at least two orthopedic fasteners are inserted into the femur, with at least one orthopedic fastener on either side of the physis. Any number of orthopedic fasteners can be used.

At step 272, an implant attacher that secures the orthopedic implant to the positioning device can release the orthopedic implant from the positioning device. In one embodiment, the implant attacher can be unthreaded from the orthopedic implant, thereby freeing the positioning device from the orthopedic implant.

At step 274, the positioning device is removed from the patient.

Figure 3:
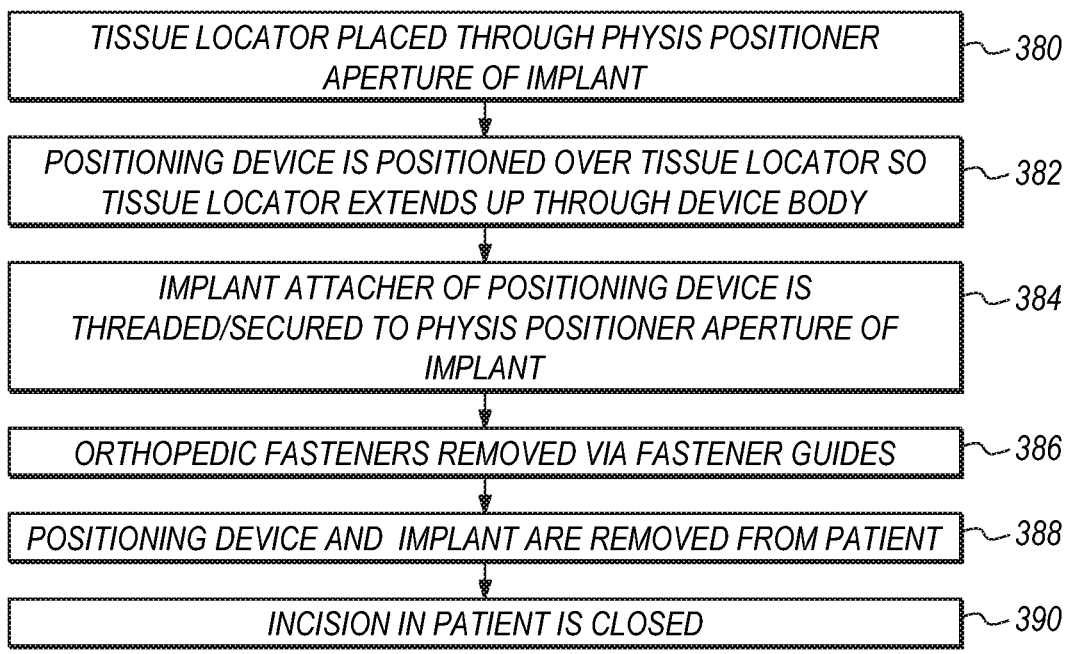
FIG. 3 is a flow chart describing one embodiment of a method for surgical implant removal.

FIG. 3 is a flow chart describing a method for surgical implant removal. It is understood that the methods described herein may include additional steps that are not specifically described. Further, the methods described herein may include steps that are described that can be omitted. In one embodiment, the method can include one or more of the following steps.

At step 380, a tissue locator is placed through a physis positioner aperture of the orthopedic implant via an incision in the patient.

At step 382, an orthopedic implant positioning device can be positioned over the tissue locator so that the tissue locator extends up through a device body of the positioning device.

At step 384, an implant attacher of the positioning device can be threaded into the physis positioner aperture to secure the orthopedic implant to the positioning device.

At step 386, each of the orthopedic fasteners that hold the orthopedic implant to the femur can be removed via corresponding fastener guides in the device body of the positioning device.

At step 388, the positioning device and the orthopedic implant can be concurrently removed from the patient.

At step 390, the incision of the patient can be closed.

The process of positioning the plate quickly and effectively with minimal image exposure and tissue sparing retraction is difficult and time consuming. With the orthopedic implant positioning systems disclosed herein, various orthopedic implants can be installed and/or removed for various fractures, including but not limited to, distal fibular fractures, distal radius fractures, radial shaft fractures, femoral shaft fractures, humeral shaft fractures and the like.

It should be noted that, as used in this specification and the appended claims, the singular forms "a," "an," and "the" include plural referents unless the content and/or context clearly dictates otherwise. It should also be noted that the term "or" is generally employed in its sense including "and/or" unless the content or context clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as arranged and configured, constructed and arranged, constructed, manufactured and arranged, and the like.

The headings used herein are provided for consistency with suggestions under 37 CFR 1.77 or otherwise to provide organizational cues. These headings shall not be viewed to limit or characterize the invention(s) set out in any claims that may issue from this disclosure. As an example, a description of a technology in the "Background" is not an admission that technology is prior art to any invention(s) in this disclosure. Neither is the "Summary" or "Abstract" to be considered as a characterization of the invention(s) set forth in issued claims.

The embodiments described herein are not intended to be exhaustive or to limit the invention to the precise forms disclosed in the following detailed description. Rather, the embodiments are chosen and described so that others skilled in the art can appreciate and understand the principles and practices. As such, aspects have been described with reference to various specific and preferred embodiments and techniques. However, it should be understood that many variations and modifications may be made while remaining within the spirit and scope herein.

It is understood that although a number of different embodiments of the catheter system have been illustrated and described herein, one or more features of any one embodiment can be combined with one or more features of one or more of the other embodiments, provided that such combination satisfies the intent of the present invention.

While a number of exemplary aspects and embodiments of the catheter system have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope, and no limitations are intended to the details of construction or design herein shown.

What is claimed is:

1. A positioning device for positioning an orthopedic implant in a patient during a surgical procedure, the positioning device comprising:
    a first orthopedic fastener that is configured to penetrate into a bone of the patient to secure the orthopedic implant to the bone;
    a device body that is configured to be removably positionable at least partially subcutaneously within the patient during the surgical procedure, the device body being configured to retract tissue of the patient during the surgical procedure, the device body including a first fastener guide that is configured to guide positioning of the first orthopedic fastener relative to the bone of the patient, the device body being inflatable;
    an implant attacher configured to removably secure the orthopedic implant to the device body, the implant attacher movably extending through the device body along an attacher axis; and
    a tissue locator that movably extends through the implant attacher along the attacher axis.

2. The positioning device of claim 1 wherein the device body is configured to releasably secure the orthopedic implant during positioning of the orthopedic implant in the patient.

3. The positioning device of claim 1 wherein the first fastener guide is angled at least 3 degrees relative to the attacher axis.

4. The positioning device of claim 1 further comprising a second orthopedic fastener, and wherein the device body further comprises a second fastener guide so that the first and second fastener guides are positioned on opposing sides of the implant attacher, and wherein fastener guide is configured to guide positioning of the second orthopedic fastener relative to the bone of the patient.

5. The positioning device of claim 4 wherein the first and second fastener guides are non-parallel to one another.

6. The positioning device of claim 1 wherein the implant attacher includes threads that selectively engage the orthopedic implant to removably secure the orthopedic implant to the device body.

7. The positioning device of claim 1 wherein the orthopedic implant is a growth plate.

8. The positioning device of claim 1 wherein the first orthopedic fastener is threaded.

9. The positioning device of claim 1 wherein the device body has a somewhat frustoconical configuration.

10. The positioning device of claim 1 wherein the device body has a somewhat cylindrical configuration.

11. The positioning device of claim 1 wherein the orthopedic implant is formed from metal.

12. The positioning device of claim 1 wherein the orthopedic implant is formed from a polyester fiber material.

* * * * *